United States Patent [19]

Gorsuch

[11] Patent Number: 5,735,809
[45] Date of Patent: Apr. 7, 1998

[54] FIBER ASSEMBLY FOR IN VIVO PLASMA SEPARATION

[75] Inventor: Reynolds Gorsuch, Yountville, Calif.

[73] Assignee: Matria Healthcare, Inc., Marietta, Ga.

[21] Appl. No.: 764,631

[22] Filed: Dec. 5, 1996

[51] Int. Cl.⁶ .................................................. A61M 37/00
[52] U.S. Cl. ........................................ 604/4; 604/6; 604/53
[58] Field of Search ............................ 604/6, 53, 52, 604/4, 282

[56] References Cited

U.S. PATENT DOCUMENTS

| | | |
|---|---|---|
| 4,950,224 | 8/1990 | Gorsuch et al. . |
| 5,151,082 | 9/1992 | Gorsuch et al. . |
| 5,152,743 | 10/1992 | Gorsuch et al. . |
| 5,217,440 | 6/1993 | Frassica ..................... 604/282 |
| 5,224,926 | 7/1993 | Gorsuch et al. . |

*Primary Examiner*—Michael Buiz
*Assistant Examiner*—Julian W. Woo
*Attorney, Agent, or Firm*—Jerry R. Seiler, Esq.

[57] ABSTRACT

An improved plasma extraction element for being implanted in a blood vessel for carrying out in vivo plasma separation comprises an elongated catheter having a fan-like assembly of elongated hollow microporous polymeric fibers loops spaced apart along the outer catheter surface. According to the invention the catheter is made from a plurality of elongated arc-shaped segments, a helically wrapped elongated polymer ribbon, a flexible polymer sheet and a plurality of polymer washers.

61 Claims, 4 Drawing Sheets

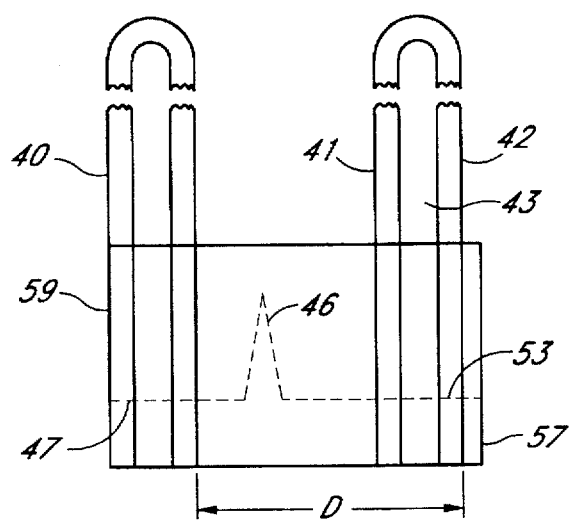
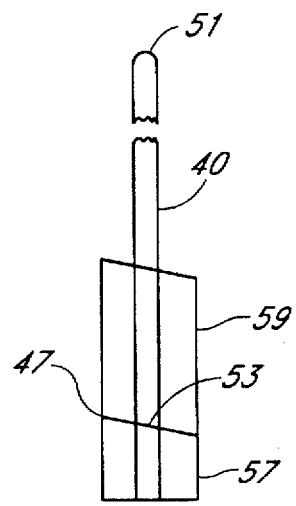
FIG.4  FIG.5
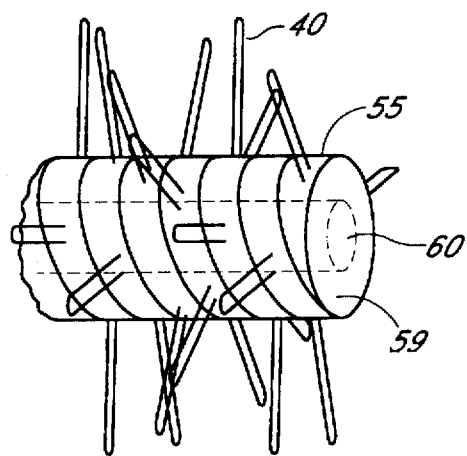
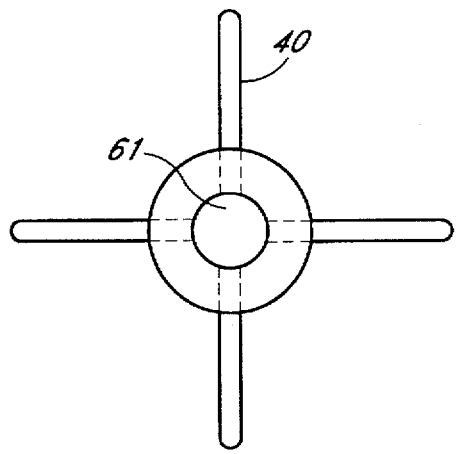
FIG.6  FIG.7

FIBER ASSEMBLY FOR IN VIVO PLASMA SEPARATION

BACKGROUND OF THE INVENTION

In U.S. Pat. No. 5,224,926 there are disclosed different embodiments of devices for being implanted in a blood vessel for carrying out continuous in vivo plasma separation. Such devices are improved designs for plasma extraction catheters incorporating a plurality of hollow elongated microporous fibers secured to an axial header and catheter for being implanted into a blood vessel of a patient. Plasma is continuously diffused through the pores of the hollow fibers which prevent cellular components larger than plasma from diffusing or entering into the hollow fiber interior. By using such hollow fibers for separating the plasma from the other blood components, the separated plasma may be treated for removing antibodies, antigens, pathogens, toxins and other undesirable materials. Methods and apparatus for carrying out such treatment are disclosed in U.S. Pat. Nos. 4,950,224, 5,152,243 and 5,151,082, all of which aforesaid patent disclosures are incorporated herein by reference.

The present invention is directed to further improvements in the designs of hollow micro fiber assemblies to be used for such in vivo plasma separation, and methods for preparing such improved fiber assemblies.

SUMMARY OF THE INVENTION

The improved fiber assemblies of the invention incorporate a fan-like assembly of elongated microporous hollow fiber loops spaced apart circumferentially and axially along a hollow elongated catheter. The present invention describes four different embodiments of such a fiber assembly configuration. The elongated catheter is prepared using a plurality of arc-shaped segments, a helically wrapped elongated polymer ribbon, a flexible polymer sheet, and plurality of polymer washers. In each of these embodiments, the elongated microporous hollow polymeric fiber loops are secured to the catheter components as will be described in further detail hereinafter.

BRIEF DESCRIPTION OF THE DRAWINGS

FIGS. 4–7 illustrate another embodiment of the hollow fiber assembly of the invention utilizing a continuous ribbon of cast polymer in which the hollow fiber loops are inserted; FIG. 4 is a side view of a portion of the fiber assembly and FIG. 5 is a front view thereof; FIG. 6 is a side view of a portion of a catheter after the continuous ribbon is wound around a mandrel and FIG. 7 is an end view taken along a plane perpendicular to the axis of the elongated catheter;

DETAILED DESCRIPTION OF THE PREFERRED EMBODIMENTS

Figure 1:
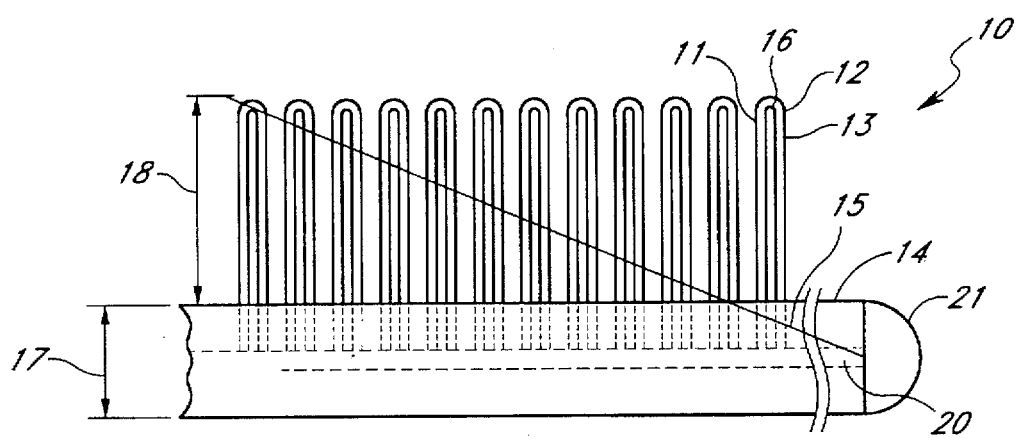
FIG. 1 is a side elevational view illustrating an embodiment of a fiber assembly of the invention with elongated microporous hollow polymeric fiber loops extending from an elongated arc-shaped catheter segment.
Figure 2:
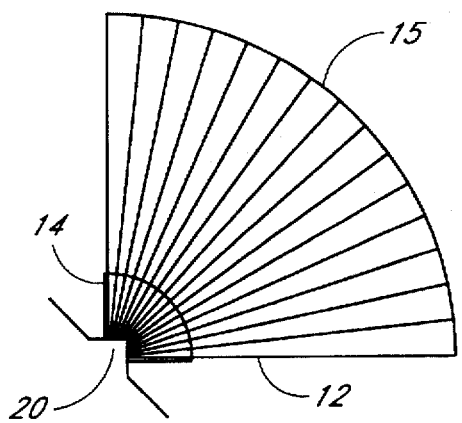
FIG. 2 is a front profile view of the arc-shaped catheter segment of FIG. 1 showing the profile of the fiber loops with the segment rotated 90° along its length to form the fan-like fiber loop profile.
Figure 3:
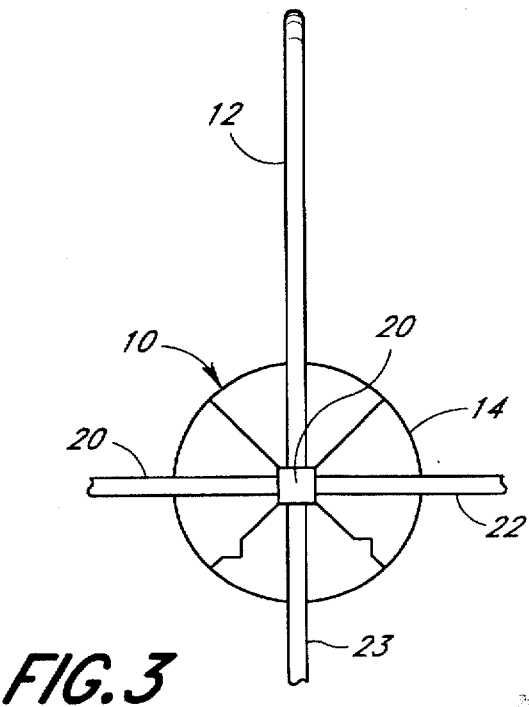
FIG. 3 is a partial front view of a catheter assembled using four 90° arc-shaped segments, showing a front fiber loop and a portion of other front fiber loops taken along a plane perpendicular to the axis of the catheter.

As used herein, the term catheter is intended to define a plasma extraction component of an assembly that typically includes a dual lumen catheter, along with a suitable interface header and terminal plug. FIGS. 1–3 illustrate an embodiment for preparing a catheter using a plurality of arc-shaped catheter segments each of which is cast with a plurality of fiber loops. Preferably, four catheter quadrants are used, each quadrant being substantially an arc-shaped catheter segment of approximately 90°, although more or fewer segments may be used to form the catheter. Where four catheter segments or quadrants are used, as illustrated in FIGS. 1–3, each catheter segment is cast with the desired number of fiber loops. Each fiber loop extends substantially perpendicular to the elongated axis of the assembled catheter. The fiber loops are preferably coterminous, i.e., substantially of equal length. Each of the fiber loops is hollow, formed of a fiber membrane as will be discussed in more detail hereinafter.

FIG. 1 shows a side view of a portion of catheter 10 with a terminal plug 21 and illustrating fiber loops along one segment 14. As shown in FIG. 1, each fiber loop 12 is composed of a pair of substantially straight elongated hollow legs 11 and 13 and an integral hollow loop 16 at the distal end connecting the two legs. The fiber loops and catheter segment are preferably cast in a centrifuge, to avoid wicking, and preferably utilizing a polyurethane to form the catheter segments. After each segment is formed, the casting is cut to form the catheter exit lumen 20 and expose the open ends of the hollow fibers which communicate with the catheter lumen. After cutting each of the castings and inspecting the open fiber ends, the four quadrants are assembled in a jig, and the distal end of each quadrant is rotated 90° clockwise and cemented to form a helical fan-like profile of fiber loops. Such a 90° fan-like profile of a catheter quadrant is illustrated in FIGS. 1 and 2. In FIG. 1, the appearance of the fiber assembly for one quadrant prior to the rotation is observed with each of the fiber loops 12 secured to the segment shown in substantially parallel alignment prior to the rotation, line 15 representing the height of the fiber profile in the direction of the observer after rotation. It will also be observed that prior to rotation each of the two legs 11 and 13 of fiber loop 12 are aligned substantially along the same plane taken along the axis of the cannula segment 14. However, the spatial relationship of the two legs may be somewhat modified after rotation of the catheter quadrant whereby the two legs of each fiber loop may be offset at least slightly from one another along the axis of the assembled cannula. Once the quadrants or segments are assembled in the jig, and each segment is rotated to form the helical fan-like profile of fiber loops, the segments are cemented together along their edges to form the catheter having a lumen 20 extending along the interior center. FIG. 2 schematically illustrates the fan-like fiber profile represented by line 15 extending along the top ends of the fiber loops of the cannula segment 14. In FIG. 3, only the front legs of four front fiber loops 12, 21, 22 and 23 are shown.

The dimensions of the catheter may be selected as may be the number of fiber loops. Preferably, the finished catheter 19 has a length of between about 2 and about 4 cm, and a diameter 17 of between about 10 and about 20 mm. The length 18 of each of the fiber loops from the surface of the catheter to the distal end is preferably between about 4 and about 8 mm. Each row of fibers in each of the 90° segments will have between about 10 and about 20 fiber loops. A typical catheter made up of 4 quadrants will have 16 fiber loops per quadrant and a fiber leg length from the surface of the catheter to the distal end of the fiber loop of 6 mm. With 16 fiber loops in a quadrant of the typical assembly described above, the center line of each loop is rotated 6° from an adjacent loop in the fan-like fiber profile. A typical catheter has a length of 2.56 cm, a diameter of 4 mm and the dimension of the lumen 20 is 1.6×1.6 mm. Each fiber loop produces 1.2 cm (6 mm×2) active fiber length, and with 4 quadrants having 16 loops each, a total active fiber length of 75 (76.8) cm is produced resulting in a plasma extraction surface of 7.5 cm$^2$. Fiber spacing is 0.4 mm and fiber O.D. is 4 mm, so that each fiber loop requires 1.6 mm linear space on the assembly.

The shape of the fiber loops may also be modified from those illustrated in FIGS. 1 and 3, to provide a hollow loop 16 having a greater or broader radius, which may be desirable to prevent folding or kinking at the loop end which could result in restricting flow within the hollow fiber. Moreover, the shape of the hollow loop is not so critical and need not be uniformly arched between the fiber legs. Thus, a more flattened, broader loop not having a uniform arc or radius may be used. Although such modified fibers would have shorter legs, or legs which are not so straight as those shown, the overall fiber length is not to be reduced and so that the effectiveness of the fibers for separating plasma is not reduced or compromised. Although the fibers shown each extend from a single catheter segment or quadrant, the structures could be modified to have one fiber leg extending from one quadrant and another leg from a different segment. Deployed, the plasma extraction assembly described above has an outer diameter of 1.6 cm, and may be folded around the catheter for insertion or removal. The finished assembled catheter and extraction assembly is preferably treated with a siloxane coating by plasma polymerization process and a co-valiantly bonded coat of heparin. Such coating is understood in the art and need not be explained further. The finished catheter is attached to a dual lumen catheter using a suitable interface header and terminal plug, and is available for use in plasma extraction as disclosed in the aforesaid patents.

In FIGS. 4–7 there is illustrated another embodiment for producing a fiber assembly of the present invention using an elongated polymer ribbon to which are attached the elongated hollow microporous polymer fiber loops. The polymer ribbon comprises a continuous ribbon of polyurethane cast with inserts of the hollow fiber membranes in the form of fiber loops and cut to form panels. FIGS. 4 and 5 illustrate a fiber ribbon 59 with hollow polymeric fiber loops 40 composed of two legs 41 and 42 separated by space 43. The continuous ribbon is preferably cast in a centrifuge to avoid wicking with the fiber loops extending through the ribbon which is then cut along line 47 to expose the open end 53 of each leg of the hollow fiber membrane loops and permit inspection of each fiber leg opening. At the time of casting, each fiber loop is approximately 15 mm long, 7.5 mm for each leg. A typical and preferred thickness of ribbon 59 is about 1 mm. With a typical casting of about 1.5 mm, a bottom piece 57 of approximately 0.5 mm is cut along line 47 from the bottom of each panel. The cut 47 is made on a bias or slant as shown in FIG. 5 to compensate for displacement effect of winding the ribbon or panel on a mandrel. A notch 46 is also cut along the bottom of each panel between adjacent fiber loops to compensate for winding the ribbon panel on a mandrel.

In a preferred or typical ribbon assembly, each fiber loop uses two fiber segments of about 0.4 mm and two spacer segments of 0.3 mm for a total linear space of 1.4 mm per loop. With a circumference of 8.56 mm and using 4 loops per turn a resulting extraction catheter has 2.14 mm panel length D available per each fiber loop as shown in FIG. 4. For such a typical panel the width of notch 46 along cut line 47 is 0.6 mm. After the panel is cut, length between the surface of the ribbon to the distal end of the fiber loop is 6 mm to produce 1.2 cm of active fiber length. The ribbon panels or segments of ribbon are assembled by winding the ribbon on a 2 mm diameter mandrel to form catheter 55 having a central axial lumen 61 as shown in FIG. 6. To achieve a preferred catheter assembly of this embodiment having a length of 1.92 cm, the catheter is formed using 16 turns of the ribbon with the fiber loops 40 spaced apart at four loops per turn as illustrated in FIG. 7. To achieve a 63 fiber loop panel requires 14 turns on a 2 mm diameter mandrel; a 60 fiber loop panel requires 16 turns. It will also be desirable and preferable to vary the length of ribbon panel allocated to each loop to offset the fiber loops from one another along the axis of the catheter, thereby increasing the fiber surface area facing the axis of blood flow in a vessel in which the catheter and assembly is used. The fibers in FIGS. 6 and 7 are shown schematically only to illustrate their general spatial relationship relative to the wound structure and without regard to size or dimensional accuracy relative to the size of the cannula.

In this embodiment, the hollow fiber loops are preferably substantially uniformly spaced along the elongated ribbon at between about 1.5 and about 3.5 mm. The most preferred spacing between the center line of elongated fiber loops is between about 2.0 mm and about 2.5 mm. The thickness of the ribbon is preferably between about 0.5 and 2.0 mm. The length of the hollow fibers is substantially uniform, between about 4 mm and about 8 mm from the catheter surface to the distal end of the fiber, with about 6 mm for each loop most preferred for a typical fiber assembly. As also shown in the drawings, the fiber legs preferably extend substantially perpendicular from the catheter surface. Moreover, as illustrated in FIG. 5, the fibers are substantially centered between the edges of the ribbon. As also illustrated in FIGS. 4 and 5, the two legs of each fiber loop are substantially parallel.

The catheter is formed by helically wrapping the ribbon around a cylindrical surface or mandrel to form a fan-like profile of each fiber loop to the axis of blood flow. The ribbon is wrapped at a pitch to form an acute angle greater than about 30° between the elongated axis of the ribbon relative to the radius of the cylinder or mandrel. Preferably, the acute angle is greater than about 45° whereby the profile of the two fiber legs of each fiber loop do not overlap and are substantially exposed along the axis of the catheter and blood flow. It will be observed in FIG. 6 that the fiber loops are helically spaced around the perimeter of the catheter. Deployed, the above-described catheter embodiment will have an O.D. of 1.6 cm. The fiber loops may be folded around the catheter for insertion, or removal. The finished assembled catheter and extraction assembly will also be treated with siloxane and coated by plasma polymerization process.

Figure 8:
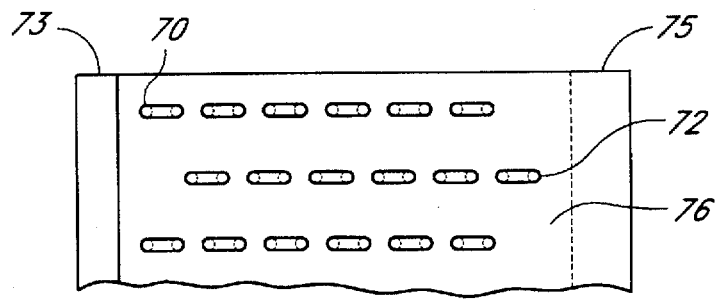
FIGS. 8 and 9 illustrate another embodiment of the invention utilizing a cast assembly of a molded plastic sheet in which rows of hollow fiber loops are secured, FIG. 8 illustrating a top view of the sheet and fiber loops and FIG. 9 a front view thereof.
Figure 9:
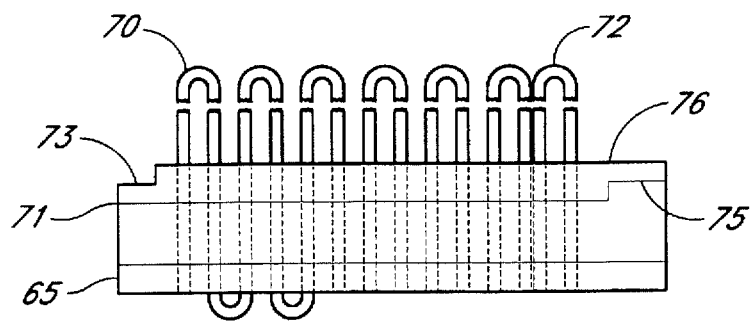

FIGS. 8 and 9 illustrate another embodiment for preparing a catheter assembly of the invention using a flat sheet cast with rows of fiber loops spaced along the sheet. FIG. 8 is a top view of a portion of a sheet 76 having a plurality of rows of fiber loops 70 extending from the top surface of the sheet. FIG. 9 is a front view of the sheet of FIG. 8 showing the cast of the sheet prior to cutting. As observed in FIG. 9, the sheet 76 is cast with a plurality of fibers which may be assembled using a horizontal wire jig positioned above a mold base 65 and threading the fibers through holes in the mold base. The holes are aligned so that the legs of the fibers threaded through the holes form the rows of fibers shown in FIG. 8. After all of the fibers are threaded into the mold base, the assembly is placed in the potting mold and centrifuged while injecting polyurethane to form the plastic sheet. Alternatively, the fibers could be formed into a ribbon assembly on a textile weaving machine and one side attached to the bottom of the mold before casting.

Figure 10:
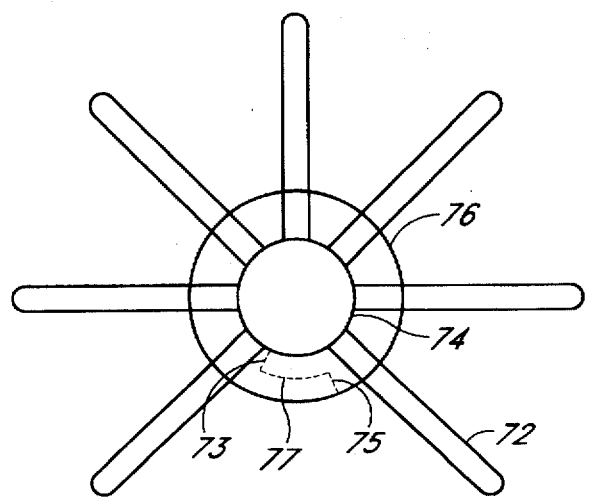
FIG. 10 illustrates an end view of the sheet panel shown in FIGS. 8 and 9 after the panel has been formed around a mandrel to prepare a catheter.

After the molded assembly has cured, the bottom of the cast is cut off along line 71 (FIG. 9) to expose the hollow fiber lumens which may then be inspected. The two edges along the sides of the cast sheet are preferably cut or notched as illustrated in FIG. 9 to form matching flaps 73 and 75 which will be mated and bonded. The flexible sheet having the rows of fiber loops is then wrapped around a mandrel, typically 2 mm in diameter, and bonded at the mating surfaces of the flaps as illustrated in FIG. 10 along bonding line 77. The rows of fibers are preferably spaced so as to expose a maximum number of fiber loops along the axis of the catheter. As also illustrated, the two legs of each of the fiber loops are preferably parallel to one another. The finished assembled catheter and extraction assembly is preferably treated with siloxane and a coat of heparin as previously discussed.

The length of the plastic sheet used in this embodiment and the resulting catheter are preferably between about 8 mm and about 20 mm, having between about 5 and about 12 rows of fibers of between about 4 and about 8 fiber loops each. The ratio of the length of the catheter to the spacing between the rows of fiber loops is between about 10:1 and about 5:1, respectively. Distance between the rows is between about 1.0 and about 3.0 mm, with the rows and the fiber loops in each row being substantially parallel and along different planes and substantially normal to the axis of the catheter. In preferred and typical catheters prepared according to this embodiment, the ratio of the length of the catheter to the spacing between rows is preferably about 8:1, respectively. Accordingly, for a 9.6 mm catheter length the spacing between rows is 1.2 mm, and for a 16 mm length spacing of 2 mm is used. Such length and spacing will provide 8 rows of fibers, although a different number of rows may be used, depending on the hollow fiber membrane surface area required for the plasma extraction. The length of each fiber loop is as disclosed in the earlier embodiments, with the typical or preferred length being about 6 mm from the surface of the catheter to the distal end of a fiber loop. FIG. 10 is a end view of a catheter cast according to the above-described embodiment showing the outer lines of seven fiber loops, six in the front row nearest the viewed end and the center line of end fiber 72 from the second row which is also exposed.

Figure 11:
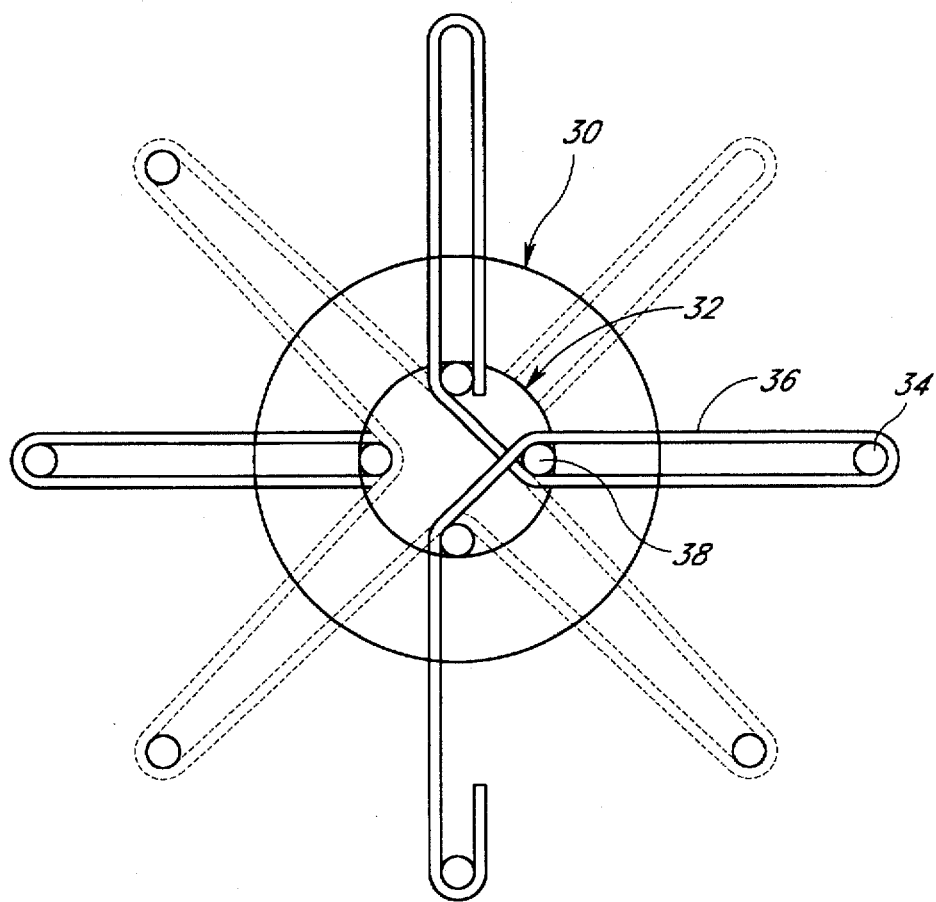
FIG. 11 is a front view of another embodiment of the invention utilizing fiber loops wound on a pin jig with washers used between layers of fiber loops to form the elongated hollow catheter fiber assembly.

In FIG. 11 there is illustrated yet another embodiment for preparing a hollow fiber plasma extraction assembly according to the present invention. In this embodiment, a plurality of washers 30 are used on a pin jig having a plurality of inside pins 38 and outside pins 34. Each of the washers are positioned with their center openings 32 around the inside pins. The hollow fiber loops are produced by winding a length of hollow fiber between the inside and outside pins.

In a preferred embodiment, four fiber loops are wound on a front side of each washer and four loops wound on the obverse or back side of each washer to form eight loops per washer. A preferred method of winding is illustrated in FIG. 11 with the four fiber loops wound on the front side and shown in solid lines and four fiber loops wound on the back side of the washer as shown in dashed lines.

Any suitable method of winding the fibers or otherwise laying them up, on the two sides of each washer may be used. In a preferred process each fiber is laid in a slot molded into the washer and glued in place. It will also be noted that in a preferred embodiment, the center line of each fiber is displaced from the other fiber approximately 45°, with the front and back fiber loops alternating. A typical embodiment uses a loop having 1.2 cm of active length, the active length being defined as the exposed length of the fiber loop or fiber loop leg from the outer edge of the washer to the distal end. With each loop producing a 1.2 cm of active length, and with eight washers used, each having eight fiber loops extending therefrom as shown in FIG. 11, each washer produces 9.6 cm of active fiber to achieve 75 cm of active fiber length for the typical catheter and plasma extraction element.

Prior to assembly, each washer has its center hole cut to remove excess fiber, thereby exposing the center lumen of each fiber loop to the plasma extraction lumen 32. The 8 washers and their fibers are then threaded on a 2 mm diameter mandril and cemented together to achieve the finished assembled catheter and extraction assembly unit. Again, the final assembly is preferably treated with siloxane coating by plasma polymerization and co-valently bonded with a coat of heparin.

The material used for the hollow fiber membrane loops described in the various embodiments above is preferably a polypropylene commercially available from Akzo-Nobel, as a micro PES hollow fiber material. Such a preferred material has a transmembrane flux (TMF) equal to or greater than 40 ml/min/cm$^2$ (H$_2$O)/bar. The outer diameter of such fibers is preferably 500 µm and an inner diameter of 300 µm, with a circumference of 0.1 cm. Such a fiber gives a surface area of 1 cm$^2$ to each 10 cm of fiber length.

The fiber assemblies disclosed above may be attached to a dual lumen 12 F catheter along with a suitable interface header and terminal plug. Such assemblies are similar to that disclosed in the aforesaid U.S. Pat. No. 5,224,926, the description of which is incorporated herein by reference. A preferred requirement of the hollow fiber membrane assemblies of the invention is to achieve an exudate of 30 ml/min of extracted plasma and having a Δ pressure across the membrane of 75 mm Hg=0.1 bar. For such a requirement a surface area is 30 ml/min/(40 ml/min×0.1 bar)=7.5 cm$^2$ fiber and having an active fiber length of 75 cm total. Although typical dimensions as well as ranges have been disclosed, the dimensions may be vary depending on the size of the patient on which it is to be used as well as the specific vessels in which the assembly is to be inserted. For example, a typical adult vena cava is approximately 25 mm diameter whereas veins in the upper respiratory area typically have a diameter of 6–10 mm. As previously noted, the shapes of the fibers may be modified from those shown, whereby the loops may be broadened, and legs shortened, so long as the overall fiber lengths are not reduced. In addition, it may also be advantageous to use a mix of fiber shapes, such as mixing fibers having longer legs, and smaller radius loops with those having shorter legs and larger or more flattened loops, and alternating such shapes to minimize or avoid a shadow effect of adjacent fibers having the same fiber profile. Thus, such variations may be considered in producing plasma extraction catheters of the aforesaid designs having different dimensions, numbers of fiber loops, etc., within the ranges given herein as will be understood by those skilled in the art.

What is claimed is:

1. A fiber assembly for being implanted in a blood vessel for carrying out in vivo plasma separation comprising:
an elongated hollow catheter having a circumferential fan-like assembly of elongated microporous hollow polymeric fiber loops spaced apart circumferentially and axially, each fiber loop extending substantially radially from the outer surface of said elongated catheter with the interior of each said hollow fiber communicating with the lumen of said catheter, and wherein said catheter comprises a plurality of elongated arc-shaped segments joined axially along said lumen, each of said segments having a plurality of said elongated fiber loops extending radially therefrom.

2. A fiber assembly of claim 1 wherein said fan-like assembly of fiber loops comprises one or more helical rows of said fiber loops extending along the length of said elongated hollow catheter.

3. A fiber assembly of claim 2 wherein each of said arc-shaped segments comprises a single helical row of said fiber loops.

4. A fiber assembly of claim 1 wherein each said fiber loop comprises a pair of substantially straight, elongated, legs having an integral hollow loop extending between said legs at the distal end thereof.

5. A fiber assembly of claim 2 wherein each said fiber loop comprises a pair of substantially straight, elongated, legs having an integral hollow loop extending between said legs at the distal end thereof.

6. A fiber assembly of claim 1 wherein a radial centerline of adjacent fiber loops are separated circumferentially between 2° and 10°.

7. A fiber assembly of claim 1 wherein the radial centerline of adjacent fiber loops are separated circumferentially between 4° and 8°.

8. A fiber assembly of claim 1 comprising four of said segments, each segment covering a circumferential arc of approximately 90°, each segment having between 10 and 20 of said fiber loops thereon.

9. A fiber assembly of claim 2 comprising four of said arc-shaped segments, each segment covering a circumferential arc of approximately 90°, and each of said helical rows having between 10 and 20 of said fiber loops therein.

10. A fiber assembly of claim 3 comprising four of said arc-shaped segments, each segment covering a circumferential arc of approximately 90°, and each of said helical rows having between 10 and 20 of said fiber loops therein and wherein each said helical row of fibers covers an arc of approximately 90°.

11. A fiber assembly of claim 1 having between about 4 and about 8 of said fiber loops per centimeter of catheter length.

12. A fiber assembly of claim 2 having between about 4 and about 8 of said fiber loops per centimeter of catheter length.

13. A fiber assembly of claim 1 comprising four of said segments, each said segment having 16 of said fiber loops thereon and wherein the centers of adjacent fiber loops are separated circumferentially approximately 6°.

14. A fiber assembly of claim 13 wherein the length of each of said fiber loops is between about 4 mm and about 8 mm.

15. A fiber assembly of claim 10 wherein each said fiber loop comprises a pair of substantially straight, elongated, legs having an integral hollow loop extending between said legs at the distal end thereof.

16. A fiber assembly of claim 1 wherein said fiber loops are substantially circumferentially coterminous.

17. A fiber assembly of claim 15 wherein said fiber loops are substantially circumferentially coterminous.

18. A fiber assembly of claim 1 wherein the diameter of said assembly is between 10 and 20 mm.

19. A fiber assembly of claim 1 wherein the diameter of said assembly is between 15 mm and 17 mm.

20. A fiber assembly of claim 15 wherein the diameter of said assembly is between 15 mm and 17 mm.

21. A fiber assembly of claim 1 wherein the length of said assembly is between 2 cm and 4 cm, and wherein said hollow fiber loops are generally uniformly spaced along said length.

22. A fiber assembly of claim 15 wherein the length of said assembly is between 2 cm and 4 cm, and wherein said hollow fiber loops are generally uniformly spaced along said length.

23. A fiber assembly of claim 1 wherein said fibers comprise a polymeric membrane having a transmembrane flux of at least 40 ml/min/cm$^2$(H$_2$O)/bar.

24. A fiber assembly of claim 1 wherein said catheter comprises polyurethane.

25. A fiber assembly of claim 2 wherein said legs are substantially parallel.

26. A method of preparing a fiber assembly of claim 1 comprising casting each of said plurality of elongated axial segments in a centrifugal mold using a plastic, with first ends of said elongated hollow fiber loops embedded in said plastic and second distal ends extending outwardly therefrom, removing the casts of said elongated segments from said mold and cutting said casting to expose the embedded ends of said hollow fiber loops, rotating each said segment axially to form a fan-like row of said fiber loops, and joining a plurality of said segments to form said elongated hollow catheter.

27. A fiber assembly for being implanted in a blood vessel for carrying out in vivo plasma separation comprising an elongated polymer ribbon helically wrapped to form an elongated hollow catheter and having a plurality of elongated hollow microporous polymeric fiber loops extending outwardly therefrom, each of said hollow fiber loops comprising first and second elongated hollow legs joined by an integral hollow loop at the distal end thereof and wherein the hollow interior of each leg of said fiber loop communicates with the lumen of said catheter.

28. A fiber assembly of claim 27 wherein said polymer ribbon is formed along an elongated axis and wherein said first and second legs of each fiber loop are substantially parallel to one another along the elongated axis of said ribbon.

29. A fiber assembly of claim 28 wherein said first and second fiber legs of each said fiber loop are spaced apart and whereby said polymer ribbon is helically wrapped around a cylindrical surface at a pitch to form an acute angle greater than about 30° between the elongated axis of said ribbon and the radius of the cylinder.

30. The fiber assembly of claim 29 wherein said acute angle is greater than about 45° and whereby the profile of the first and second legs of each fiber loop along the axis of said catheter do not overlay.

31. A fiber assembly of claim 30 wherein said hollow fiber loops are substantially uniformly spaced along said elongated ribbon at between about 1.5 mm and about 3.5 mm.

32. A fiber assembly of claim 28 wherein the thickness of said ribbon is between about 0.5 mm and about 2.0 mm.

33. A fiber assembly of claim 28 wherein the length of said hollow fibers is substantially uniform and between about 4 mm and about 8 mm between said catheter and said distal end.

34. A fiber assembly of claim 31 wherein the length of said hollow fibers is substantially uniform and between about 4 mm and about 8 mm between said catheter and said distal end.

35. A fiber assembly of claim 30 wherein said hollow fiber loops are substantially uniformly spaced along said elongated ribbon at between about 2.0 mm and about 2.5 mm, wherein the thickness of said ribbon is approximately 1 mm and wherein the length of said hollow fibers between said ribbon and said distal fiber end is approximately 6 mm.

36. A fiber assembly of claim 27 wherein said ribbon comprises polyurethane, and wherein said hollow fiber loops comprise a polymeric membrane having a transmembrane flux of at least 40 ml/min/cm$^2$(H$_2$O/bar.

37. A fiber assembly of claim 27 wherein said first and second legs are substantially perpendicular to the catheter surface.

38. A fiber assembly of claim 37 wherein said legs are substantially centered between edges of said ribbon.

39. A fiber assembly of claim 38 wherein said catheter is formed along an axis and said first and second legs of each fiber loop are substantially parallel to one another along a plane substantially normal to said axis.

40. A fiber assembly of claim 39 wherein each of said substantially parallel rows lie along a different plane substantially normal to said axis.

41. A fiber assembly of claim 40 wherein the distance between said rows is between about 1.0 mm and about 3.0 mm.

42. A fiber assembly of claim 31 wherein the length of said catheter is between about 8.0 mm and about 20 mm.

43. A fiber assembly of claim 41 wherein the ratio of the length of said catheter to the spacing between said rows is between about 10:1 and about 5:1, respectively.

44. A fiber assembly of claim 43 having between about 4 and about 8 of said fiber loops per row.

45. A fiber assembly for being implanted in a blood vessel for carrying out in vivo plasma separation comprising:

an elongated hollow catheter having a circumferential fan-like assembly of elongated microporous hollow polymeric fiber loops spaced apart circumferentially and axially, each fiber loop extending substantially radially from the outer surface of said elongated catheter with the interior of each said hollow fiber communicating with the lumen of said catheter, and wherein said catheter comprises a flexible polymer sheet having a plurality of rows of said hollow polymeric fiber loops extending from a first surface thereof and wherein the interior of said hollow fiber loops are exposed on a second opposite surface of said sheet, wherein said sheet is wrapped around a mandrel to form said catheter having said elongated fiber loops extending radially therefrom.

46. A fiber assembly of claim 45 wherein said sheet and said catheter has a length of between about 8 mm and about 20 mm.

47. A fiber assembly of claim 46 having between about 5 and about 12 rows of fiber loops.

48. A fiber assembly of claim 47 wherein each row contains between about 4 and about 8 fiber loops.

49. A fiber assembly of claim 48 wherein said rows of fiber loops are substantially parallel and said fiber loops in adjacent rows are offset from one another along the axis of said catheter.

50. A fiber assembly of claim 49 wherein the ratio of the length of said catheter to the spacing between rows of fiber loops is between about 10:1 and about 5:1, respectively.

51. A fiber assembly for being implanted in a blood vessel for carrying out in vivo plasma separator comprising:

a plurality of annular segments aligned along a common axis and joined therealong to form an elongated catheter, each said segment comprising a polymer washer having a first side and an opposite second side, and a plurality of elongated hollow microporous polymeric fiber loops secured to said first and second sides of said washer and extending radially from the outer peripheral edge thereof, said fiber loops being separated from one another circumferentially around the periphery of said washer, said catheter having a lumen extending axially along the center of said segments.

52. A fiber assembly of claim 51 wherein each of said segments comprise first fiber loops secured along a first side of a washer and second fiber loops secured along a second side thereof, and wherein first and second fiber loops alternate circumferentially around said assembly.

53. A fiber assembly of claim 51 wherein said fiber loops are substantially circumferentially coterminous.

54. A fiber assembly of claim 52 wherein said fiber loops are substantially circumferentially coterminous.

55. A fiber assembly of claim 51 having eight fiber loops per washer.

56. A fiber assembly of claim 55 comprising eight of said segments.

57. A fiber assembly of claim 51 wherein the diameter of said assembly is between 10 mm and 20 mm.

58. A fiber assembly of claim 53 wherein the diameter of said assembly is between 15 mm and 17 mm.

59. A fiber assembly of claim 54 having eight fiber loops per washer and wherein the diameter of said assembly is approximately 16 mm.

60. A fiber assembly of claim 51 wherein said fiber loops are generally uniformly spaced around said assembly.

61. A fiber assembly of claim 59 wherein the diameter of said washers is approximately 4 mm.

\* \* \* \* \*